United States Patent
Sweeney et al.

(10) Patent No.: US 6,285,909 B1
(45) Date of Patent: *Sep. 4, 2001

(54) PRESERVING PATIENT SPECIFIC DATA IN IMPLANTABLE PULSE GENERATOR SYSTEMS

(75) Inventors: Robert J. Sweeney, Woodbury; Brian Brandell, Minneapolis; Bruce H. KenKnight, Maple Grove, all of MN (US)

(73) Assignee: Cardiac Pacemakers, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/321,254

(22) Filed: May 27, 1999

(51) Int. Cl.$^7$ .................................... A61N 1/362
(52) U.S. Cl. ................................................ 607/32
(58) Field of Search ...................... 607/9, 60, 32, 607/30, 27

(56) References Cited

U.S. PATENT DOCUMENTS

| | | | |
|---|---|---|---|
| 3,985,123 | 10/1976 | Herzlinger et al. | 128/2.05 F |
| 3,991,747 | 11/1976 | Stanly et al. | 128/2.06 R |
| 4,129,125 | 12/1978 | Lester et al. | 128/2.05 R |
| 4,289,141 | 9/1981 | Cormier | 128/713 |
| 4,318,412 | 3/1982 | Stanly et al. | 128/696 |
| 4,428,381 | 1/1984 | Hepp | 128/715 |
| 4,458,693 | 7/1984 | Badzinski et al. | 128/715 |
| 4,531,527 | 7/1985 | Reinhold, Jr. et al. | 128/696 |
| 4,562,841 | 1/1986 | Brockway et al. | 128/419 PG |
| 4,585,008 | 4/1986 | Jarkewicz | 128/654 |
| 4,625,730 | 12/1986 | Fountain et al. | 128/419 D |
| 4,641,328 | 2/1987 | Fujise et al. | 378/8 |
| 4,688,168 | 8/1987 | Gudaitis et al. | 364/200 |
| 4,799,493 | 1/1989 | DuFault | 128/705 |
| 4,869,252 | 9/1989 | Gilli | 128/419 PG |
| 4,940,054 | 7/1990 | Grevis et al. | 128/419 |
| 4,958,632 | 9/1990 | Deggan | 128/419 PG |
| 4,998,974 | 3/1991 | Aker | 128/419 PG |
| 5,007,427 | 4/1991 | Sukuki et al. | 128/659 |
| 5,027,824 | 7/1991 | Dougherty et al. | 128/702 |
| 5,063,928 | 11/1991 | Grevis et al. | 128/419 D |
| 5,074,301 | 12/1991 | Gill | 128/419 |
| 5,111,818 | 5/1992 | Suzuki et al. | 128/644 |
| 5,117,825 | 6/1992 | Grevious | 128/419 PG |
| 5,127,404 | 7/1992 | Wyborny et al. | 128/419 P |
| 5,144,947 | 9/1992 | Wilson | 128/419 PG |
| 5,161,527 | 11/1992 | Nappholz et al. | 128/419 PG |
| 5,178,140 | 1/1993 | Ibrahim | 128/419 D |
| 5,181,511 | 1/1993 | Nickolls et al. | 128/419 PG |
| 5,183,040 | 2/1993 | Nappholz et al. | 128/419 PG |
| 5,184,615 | 2/1993 | Nappholz et al. | 128/419 |
| 5,203,326 | 4/1993 | Collins | 128/419 PG |
| 5,215,081 | 6/1993 | Ostroff | 128/419 |
| 5,215,083 | 6/1993 | Drane et al. | 128/419 D |
| 5,233,985 | 8/1993 | Hudrlik | 607/27 |
| 5,246,000 | 9/1993 | Ellis et al. | 607/27 |
| 5,251,621 | 10/1993 | Collins | 607/4 |
| 5,251,626 | 10/1993 | Nickolls et al. | 607/14 |
| 5,261,411 | 11/1993 | Hughes | 128/668 |

(List continued on next page.)

Primary Examiner—Scott M. Getzow
(74) Attorney, Agent, or Firm—Schwegman, Lundberg, Woessner & Kluth P.A.

(57) ABSTRACT

A method and a system for preserving patient specific data in implantable pulse generator systems. A communication link is established with a first implantable pulse generator. Electronic cardiac data contained within the first implantable pulse generator is retrieved through the communication link. The electronic cardiac data is then electronically downloaded to a second implantable pulse generator. Prior to downloading, the electronic cardiac data can be formatted into a format compatible with the second implantable pulse generator.

23 Claims, 6 Drawing Sheets

U.S. PATENT DOCUMENTS

| | | | |
|---|---|---|---|
| 5,274,549 | 12/1993 | Almasi | 364/413.07 |
| 5,292,339 | 3/1994 | Stephens et al. | 607/15 |
| 5,292,343 | 3/1994 | Blanchette et al. | 607/32 |
| 5,292,348 | 3/1994 | Saumarez et al. | 607/5 |
| 5,300,093 | 4/1994 | Koestner et al. | 607/32 |
| 5,304,931 | 4/1994 | Flamig et al. | 624/309 |
| 5,305,760 | 4/1994 | McKown et al. | 128/692 |
| 5,314,450 | 5/1994 | Thompson | 607/32 |
| 5,336,245 | 8/1994 | Adams et al. | 607/32 |
| 5,354,319 | 10/1994 | Wyborny et al. | 128/904 |
| 5,360,437 | 11/1994 | Thompson | 607/30 |
| 5,370,665 | 12/1994 | Hudrlik | 607/9 |
| 5,437,285 | 8/1995 | Verrier et al. | 128/702 |
| 5,480,411 | 1/1996 | Liu et al. | 606/230 |
| 5,524,629 | 6/1996 | Mahony | 128/661.08 |
| 5,535,753 | 7/1996 | Petrucelli et al. | 128/672 |
| 5,545,185 | 8/1996 | Denker et al. | 607/14 |
| 5,562,714 | 10/1996 | Grevious | 607/32 |
| 5,607,458 | 3/1997 | Causey, III et al. | 607/27 |
| 5,620,472 | 4/1997 | Rahbari | 607/27 |
| 5,630,835 | 5/1997 | Brownlee | 607/60 |
| 5,630,836 | 5/1997 | Prem et al. | 607/61 |
| 5,640,953 | 6/1997 | Bishop et al. | 128/630 |
| 5,647,369 | 7/1997 | Petrucelli et al. | 128/672 |
| 5,661,035 | 8/1997 | Tsien et al. | 436/63 |
| 5,662,691 | 9/1997 | Behan et al. | 607/32 |
| 5,682,899 | 11/1997 | Nashef et al. | 128/692 |
| 5,685,314 | 11/1997 | Geheb et al. | 128/700 |
| 5,687,733 | 11/1997 | McKown | 128/692 |
| 5,690,690 | 11/1997 | Nappholz et al. | 607/30 |
| 5,724,582 | 3/1998 | Pelanek et al. | 395/620 |
| 5,725,559 | 3/1998 | Alt et al. | 607/5 |
| 5,730,143 | 3/1998 | Schwarzberg | 128/710 |
| 5,735,286 | 4/1998 | Notten et al. | 128/700 |
| 5,735,797 | 4/1998 | Muzilla et al. | 600/441 |
| 5,741,316 | 4/1998 | Chen et al. | 607/61 |
| 5,752,977 | 5/1998 | Grevious et al. | 607/32 |
| 5,792,201 | 8/1998 | Causey, III et al. | 607/27 |
| 5,795,725 | 8/1998 | Buechler et al. | 435/7.1 |
| 5,800,473 | 9/1998 | Faisandier | 607/59 |
| 5,842,997 | 12/1998 | Verrier et al. | 600/518 |
| 5,843,138 | 12/1998 | Evers et al. | 607/30 |
| 5,908,392 | 6/1999 | Wilson et al. | 600/509 |
| 5,916,168 | 6/1999 | Pedersen et al. | 600/443 |
| 5,921,940 | 7/1999 | Verrier et al. | 600/518 |

PRESERVING PATIENT SPECIFIC DATA IN IMPLANTABLE PULSE GENERATOR SYSTEMS

FIELD OF THE INVENTION

The present invention relates generally to medical devices and more particularly to medical devices for preserving patient specific data programmed into and/or acquired by an implantable pulse generator.

BACKGROUND

Implantable pulse generators, such as implantable cardiac defibrillators (ICDs) and cardiac pacemakers, have evolved from basic to sophisticated electronic devices. As these implantable pulse generators evolve, the amount of cardiac data and information these devices store and rely upon to operate continues to increase. Cardiac data stored and acquired by implantable pulse generators include basic programmable values to patient specific cardiac data acquired over the life of the implantable pulse generator.

The typical life span of an implantable pulse generator range from 5 to 7 years. Factors that influence the life span of the implantable pulse generator include the size of the energy source, energy requirements for implementing the cardiac analysis algorithms of the implantable pulse generator, and how often the implantable pulse generator discharges electrical energy (e.g., how often an ICD discharges cardioversion pulses and/or defibrillation pulses). Once the energy source has been drained below a safe operating threshold, the implantable pulse generator is replaced. Implantable pulse generators are also replaced when post-operative complications (e.g., infection) arise after implantation.

Prior to being implanted into the patient, the replacement implantable pulse generator is programmed using a medical device programmer. The medical device programmer is used to establish a telemetric link with the implantable pulse generator after which programming instructions, including programmable operating values, are sent to control circuitry within the implantable pulse generator. In many cases, the programming instructions provided to the replacement implantable pulse generator are similar, if not identical, to the programming instructions that are already contained in the implantable pulse generator being replaced. Additionally, the implantable pulse generator being replaced may also contain patient-specific cardiac information, or data, that has been acquired during the life of the implantable pulse generator. Often times, this cardiac information could be useful to the replacement implantable pulse generator. Unfortunately, when the implantable pulse generator is replaced, the cardiac data contained in the implantable pulse generator is lost.

For the reasons stated above, and for other reasons stated below which will become apparent to those skilled in the art upon reading and understanding the present specification, there exists a need for preserving patient specific data stored in replaced implantable pulse generators.

SUMMARY OF THE INVENTION

The present subject matter provides a system and a method for reliably and conveniently preserving patient specific data stored in a replaced implantable pulse generator. The present subject matter allows for electronic data acquired and stored in the implantable pulse generator to be transferred to a replacement implantable pulse generator. By transferring the electronic cardiac data from one pulse generator to a replacement pulse generator, the replacement pulse generator benefits the patient by being programmed with cardiac data that has been acquired over the previous pulse generator's life. By not having to reacquire this data, the replacement pulse generator can utilize the established cardiac data by providing a more responsive and complete therapy to the patient. Finally, because many of the programmable values in the replacement pulse generator are identical in the pulse generator being replaced, the physician saves time by not having to enter this data into the replacement device.

The present subject matter allows for a communication link to be established with a first implantable pulse generator. Once the link has been established, electronic cardiac data stored in the pulse generator is retrieved through the communication link. The electronic cardiac data is then electronically downloaded to a second implantable pulse generator.

The present subject matter allows for the electronic cardiac data to be transferred between the first implantable pulse generator and the second pulse generator in several ways. For example, the electronic cardiac data is first downloaded, or transferred, from the first implantable pulse generator to a medical device programmer. The electronic cardiac data is then transferred from the medical device programmer to the second implantable pulse generator. In one embodiment, the transmission of the electronic cardiac data is done over a telemetric communication link established between the medical device programmer and the implantable pulse generator.

In an additional embodiment, after the electronic cardiac data has been downloaded from the first implantable pulse generator, the data is electronically processed in the medical device programmer into a format compatible with the second implantable pulse generator. The electronic cardiac data is then transmitted to the second implantable pulse generator.

Transfer of electronic cardiac data between any combination of the first implantable pulse generator, the second implantable pulse generator and the medical device programmer can also be accomplished using direct electrical connection between the circuitry within the devices. In one embodiment, the devices are coupled together through the use of connector lead(s) which establish an electrical connection between the devices and thus a higher-speed for transferring the data. The electronic cardiac data is then electronically downloaded from the first implantable pulse generator to the medical device programmer, and/or from the medical device programmer to the second implantable pulse generator by directly transferring the electronic cardiac data across the electrical connection. The cardiac data is then transferred through the use of at least one high-speed datalink.

DETAILED DESCRIPTION

In the following detailed description, reference is made to the accompanying drawings which form a part hereof and in which is shown by way of illustration specific embodiments in which the invention can be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

The embodiments illustrated herein are demonstrated in an implantable pulse generator. As used herein, implantable pulse generators include cardiac defibrillator (ICD), which may include numerous defibrillation, pacing, and pulse generating modes known in the art, and cardiac pacemakers. However, these embodiments are illustrative of some of the applications of the present system, and are not intended in an exhaustive or exclusive sense. The concepts described herein are also useful with other implantable pulse generator systems, such as cardiac pacemakers, and implantable medical device systems that stores, acquires and determines data in the course of its operation.

The present subject matter allows for electronic cardiac data acquired and stored in an implantable pulse generator to be transferred to a replacement implantable pulse generator. Initially, the electronic cardiac data stored in the implantable pulse generator is retrieved. The electronic cardiac data is then transferred to a replacement implantable pulse generator. In one embodiment, moving electronic cardiac data to a replacement device is useful in the situation where a device is being replaced for traditional reasons (e.g., when the implanted device approaches its end of life). Additionally, moving electronic cardiac data to a replacement device is useful when the device is being replaced for other less traditional reasons (e.g., infection or device failure).

One way of transferring electronic cardiac data between two implantable pulse generators is to use telemetry communication channels built into the electronic circuitry of the implantable pulse generators. In one embodiment, a medical device programmer is used to establish a telemetric link with the implantable pulse generator to be replaced. Electronic cardiac data is transferred from the implantable pulse generator to the medical device programmer over the telemetric link. The medical device programmer is then used to establish a telemetric link with a replacement implantable pulse generator. Some or all of the electronic cardiac data extracted from the implantable pulse generator to be replaced is then transferred to the replacement implantable pulse generator. The replacement implantable pulse generator then uses the transferred electronic cardiac data in performing its operations.

The present subject matter is useful for transferring electronic cardiac data between implantable pulse generators, such as implantable cardioverter-defibrillators (ICDs) and cardiac pacemakers. Programs within these pulse generators often require specific cardiac information which cannot be reliably acquired during a patient's typical visit to the physician. In addition, as implantable pulse generators become more sophisticated, cardiac information used by the pulse generators must be developed over long periods of time. Once again, this type of information cannot be reliably acquired during a patient's typical visit to the physician. Thus, transferring electronic cardiac data from one implantable pulse generator to a replacement implantable pulse generator is important for maintaining patient specific cardiac information which is useful in the operation of the replacement pulse generator.

In one embodiment, the electronic cardiac data acquired and stored by the implantable pulse generator includes at least two types of patient specific data. These patient specific data include data generated from cardiac signals sensed and utilized by the implantable pulse generator. The first type of patient specific data relates to the electrophysiologic history of the patient acquired over the life of the implantable pulse generator. Cardiac data of this type is a record of diagnostically significant information for the physician. In addition, this cardiac data can also be used to improve automated or physician directed diagnosis and treatment of pathophysiologic conditions in the patient by allowing the long term trends in the patient's electrophysiologic history to be considered, instead of the just the current cardiac state.

A second type of patient specific data relates to the manner with which the implantable pulse generator interacts with the individual patient. One example is the unique characteristics of the electrophysiologic signals sensed from the patient. These characteristics are determined by factors such as the patient's anatomy, the type and actual placement of electrodes within and/or on the heart, and by the characteristics of the patient's cardiac conduction system. The factors combine to produce the electrophysiological signals the implantable pulse generator senses during normal and abnormal cardiac activity.

An additional example of the second type of patient specific data include those that results from adaptive or "learning" features of the implantable pulse generator. For instance, the implantable pulse generator, such as a pacemaker, can use sensed cardiac information (e.g., activity, minute ventilation, stroke volume, etc.) to adjust a pacing rate in an effort to improve a patient's cardiac performance. In an additional example, cardioverter-defibrillators are programmed to predict the onset, and/or prevent and/or treat an arrhythmia that is "learned" over time by identifying relationships between markers for an arrhythmia, the occurrence of the arrhythmia and the results of different treatments for the arrhythmia. Other types of patient specific data can include data related to, or generated from, accelerometers, sensed acoustic signals, respiration, blood flow and blood pressure, time of day data was recorded, vessel diameter, autonomic nervous activity, blood pH, blood oxygen levels, blood electrolyte levels, and other data known in the art that can be recorded and stored.

For both types of patient specific data, the implantable pulse generator must store the data in memory. When the implantable pulse generator is replace, however, this patient specific cardiac data is lost. Thus, the replacement implantable pulse generator begins operation without the benefit of the cardiac data acquired by the predecessor device. The present subject matter allows patient specific cardiac data to be electronically passed, or transferred, from the implantable pulse generator to the replacement implantable pulse generator so that it is not lost at the time of device replacement.

Figure 1:
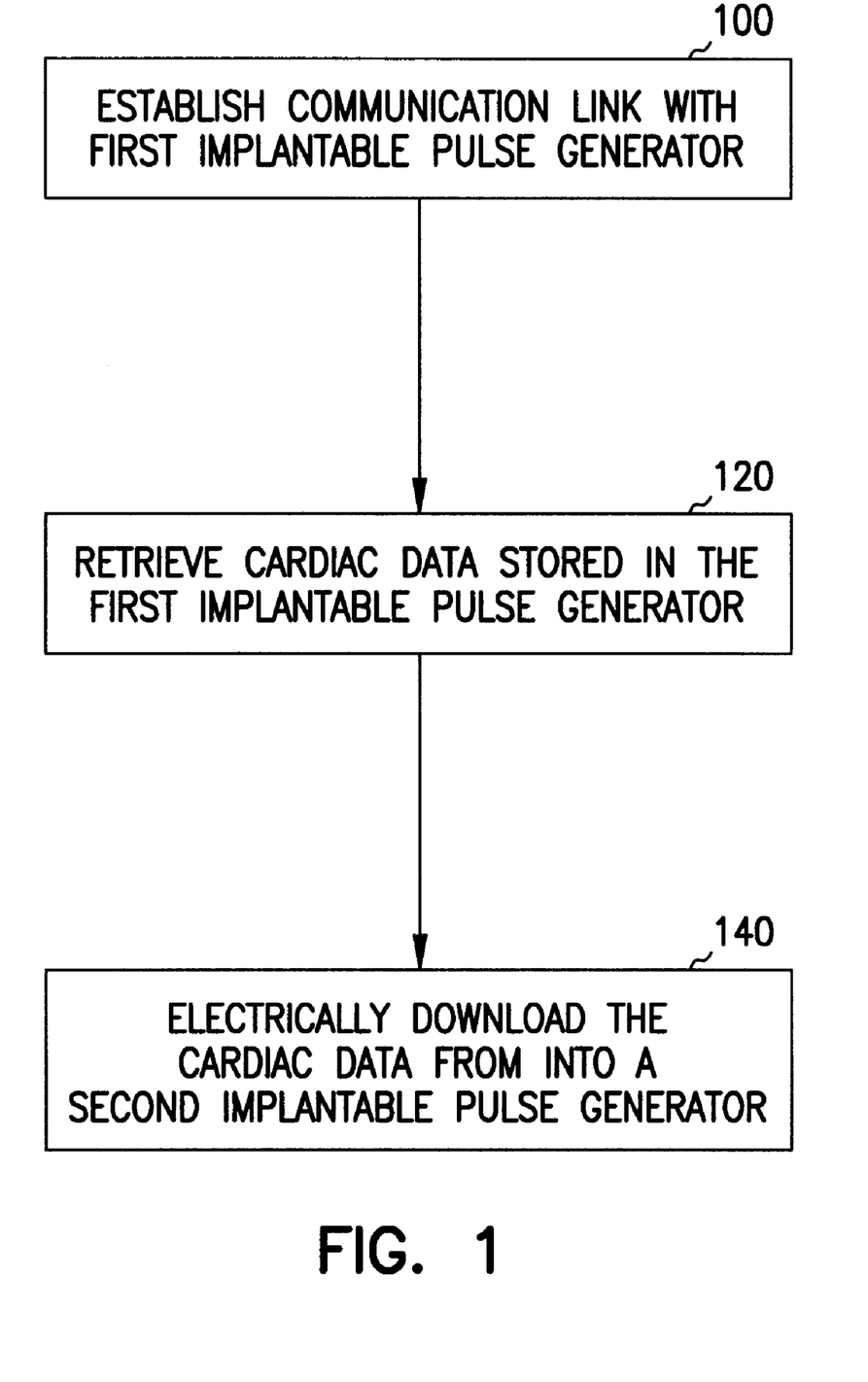
FIG. 1 is a flow chart illustrating one embodiment of the present subject matter.

Referring now to FIG. 1, there is shown an embodiment of the present subject matter. At 100, a communication link is established with a first implantable pulse generator. In one embodiment, the communication link allows for a memory circuit of the first implantable pulse generator to be searched for the presence of electronic cardiac data. In an additional embodiment, other electronic circuits in the first implantable pulse generator that store electronic cardiac data are also searched for the presence of electronic cardiac data useful for operating the replacement implantable pulse generator. In one embodiment, electronic cardiac data stored in the first implantable pulse generator includes the patient specific information previously discussed. In addition, the electronic cardiac data can also include implantable pulse generator operational parameters and specific patient information programmed into the pulse generator by the patient's physician during the life the of device. For example, these could include "templates" of a patient's normal and abnormal beats, long term history and/or circadian trends of the electrophysiologic data (e.g., average RR intervals, RR variability, QT intervals, QT variability, QRS durations, percent premature beats, percent abnormal beats).

After the communication link has been established and the electronic cardiac data for transfer has been identified, the cardiac data is retrieved from the first implantable pulse generator at 120. The electronic cardiac data from the first implantable pulse generator is then transfer to the second implantable pulse generator at 140. Once transferred, the electronic cardiac data can be used in the operation of the second implantable pulse generator.

In one embodiment, the patient specific data transferred between the first implantable pulse generator and the second implantable pulse generator can be viewed as one or more blocks of digital data. For the purpose of the disclosed embodiments, the patient specific data will be treated as one block of digital data. However, it is understood that the digital data might be more logically organized into two or more blocks of digital data of various sizes, where each block of digital data is associated with a different type of patient specific data.

Figure 2:
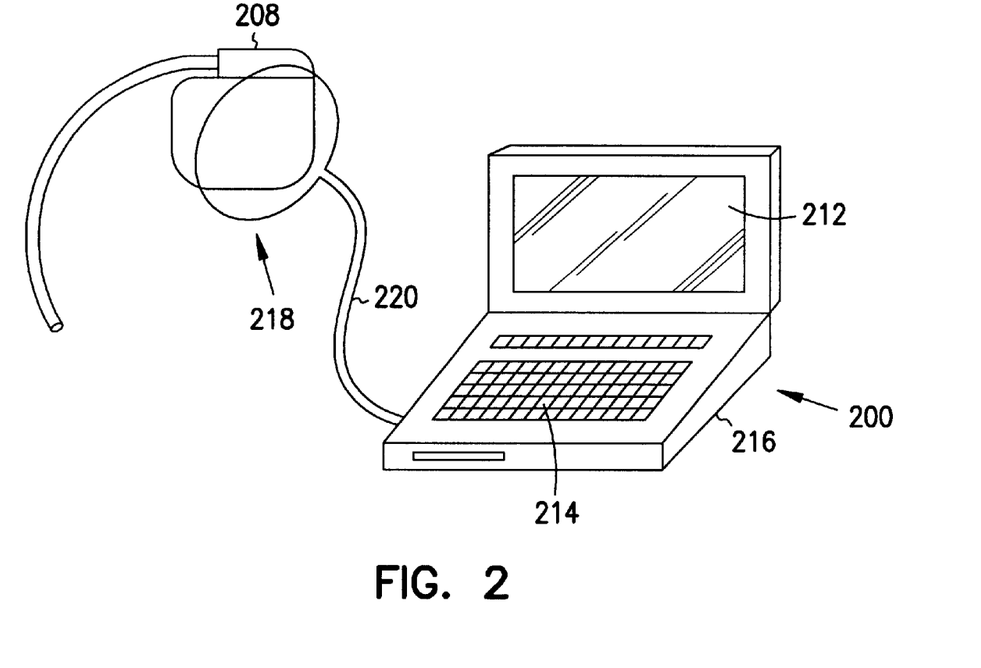
FIG. 2 is a schematic view of an implantable pulse generator in telemetric communication with a medical device programmer according to one embodiment of the present subject matter.

Referring now to FIG. 2, there is shown one embodiment of establishing a communication link with the first implantable pulse generator. In one embodiment, the communication link is established through the use of a medical device programmer 200, such as a external pacemaker or defibrillator programmer. In one embodiment, the medical device programmer 200 communicates with the first implantable pulse generator 208 via a radio frequency telemetry link. In one embodiment, the first implantable pulse generator 208 is either an implantable cardioverter-defibrillator or a cardiac pacemaker.

In one embodiment, the medical device programmer 200 comprises an outer housing 216 which is made of a thermal plastic or other suitable lightweight durable material. The medical device programmer 200 has electronic circuitry, including a communication circuit, a cardiac-data-processing circuit, and a control circuit, and a microprocessor and related circuitry, such as digital memory, which is coupled to a display screen 212. The display screen 212 is disposed on the upper surface of housing 216. The display screen 212 folds down into a closed position when medical device programmer 200 is not in use, thereby reducing the size of medical device programmer 200 and protecting the display surface of display screen 212 during transportation and storage. In an additional embodiment, the external programmer additionally has a floppy disk drive and a hard drive disposed within the housing. Air vents are provided at various points in the housing 216 so that an internal fan can circulate air within the housing 216 and prevent overheating of components therein.

The medical device programmer 200 is shown with the display screen 212 positioned in one of a plurality of possible open positions such that a display on the display screen 212 is visible to a user situated in front of the medical device programmer 200. In one embodiment, the display screen 212 is of the LCD or electroluminescent type. The display screen 212 is operatively coupled to the electronic circuitry disposed with the housing 216 and is adapted to provide a visual display of graphics and/or data under control of the programmer electronic circuitry.

The medical device programmer 200 further includes a user input device coupled to the electronic circuitry. In one embodiment, the user input device is the display screen 212, which is provided with touch-sensitive capability, such that a user can interact with the programmer electronic circuitry by touching the display area on the display screen 212 with a stylus (not shown), or even the user's finger. Alternatively, the medical device programmer 200 may be equipped with a conventional computer "mouse"-type pointing device, rather than a stylus. In the absence of either a stylus or a mouse, on-screen cursor control for enabling user interaction with medical device programmer 200 may be facilitated through a keyboard input 214 disposed on the medical device programmer 200.

The medical device programmer 200 further includes a programming head 218 coupled to the communication circuit within the programmer 200 through cable 220. The communication circuit allow the medical device programmer to receive and transmit control commands, program instructions and electronic cardiac data to, from and between implantable pulse generators. In one embodiment, the communication circuit is a radio frequency receiver/transmitter located in the implantable pulse generator 208. The programmer head 218 is place over the first implantable pulse generator 208 and the control circuit controls the communication circuit to establish a telemetry link between the first implantable pulse generator 208 and the medical device programmer 200. In one embodiment, the telemetry link between the first implantable pulse generator 208 and the medical device programmer 200 allows the electronic circuitry coupled to the graphics display screen 212 to be coupled to the electronic control circuitry of the first implantable pulse generator 208. Additionally, the telemetric contact with the implantable pulse generator 208 allows the medical device programmer 200 to retrieve and store recorded electronic cardiac data, including patient specific data, contained within the implantable pulse generator 208. The retrieved electronic cardiac data can then be displayed on the graphics display screen 212.

In one embodiment, the electronic cardiac data transfer from the implantable pulse generator 208 to the medical device programmer 200 is accomplished as a block transfer. The block transfer of data can take place with, or without, compression of the electronic cardiac data. Additionally, checksum and/or redundancy information is processed by the pulse generator 208 and the medical device programmer 200 to ensure that the data transfer operation is occurring without error.

Once the medical device programmer 200 has been used to retrieve the electronic cardiac data from the first implantable pulse generator the electronic cardiac data is stored in the memory circuit of the medical device programmer 200 while the replacement of the first implantable pulse generator takes place. Alternatively, the electronic cardiac data is transferred from the pulse generator 208 before or after the replacement of the pulse generator. However, a consideration of removing the patient specific data too long before or after the replacement of the pulse generator is that the patient specific data (or the ability to continue to adapt) would be lost during the transition period.

After the electronic cardiac data has been retrieved from the first pulse generator 208, the telemetric link with the first implantable pulse generator is broken. The cardiac-data-processing circuit is then used to format the electronic cardiac data received from the first implantable pulse generator to a format compatible with a second implantable pulse generator. The medical device programmer 200 can then be used to establish a telemetric link with the second implantable pulse generator (not shown). Once the telemetric link is established, some or all of the electronic cardiac data is transferred, or downloaded, to the second implantable pulse generator.

The size of the data block(s) transferred between the medical device programmer and the implantable pulse generator can be very large. Depending on their size, the time required to transfer the data by a telemetry link can be significant. Because the transfer of the patient specific data will typically occur during the replacement procedure of the first pulse generator, it is expected that both the first and second pulse generators will be directly accessible to the external device at some time during the procedure. Because both the first and the second pulse generators are directly accessible, a direct electrical link over which cardiac data can be transmitted and received can be established between the two implantable pulse generators through connector ports located in the header of the pulse generators.

In one embodiment, when the first pulse generator, second pulse generators and external programmer are accessible together, two of the connectors in the headers of the pulse generators (or one connector having two electrical contacts) are configured for allowing direct data transfer between the first and second pulse generators. Then, electronics internal to the second pulse generator (the device to receive the patient specific data) provide for a mode of operation where communication with the first pulse generator can occur directly through cables coupled to the first and second pulse generators.

In this embodiment, the direct connection between the first and second pulse generator is a high-speed connection over which data can be transferred. In one embodiment, transfer of data between the first and second pulse generators coupled in this manner is under the control of the external programmer. One example of providing control to one or both of the pulse generators is through a telemetric link with one of the first or second pulse generators. Alternatively, transfer of data between the first and second pulse generators is under the control of could be under partial control of either the first or second pulse generator. With respect to the high-speed connection, high-speed connections for telemetry links can include those having data transfer rates of between approximately 32,000 to 300,000 bits/second. High-speed connections for direct links can include even greater transfer rates, such as transfer rates of greater than approximately 300,000 bits/second.

Regardless of the manner in which the patient specific data is to be transferred (generator-programmer-generator or generator-generator), basic information relating to the patient specific information must be assessed. For example, before the transfer it must be established whether the transfer of patient specific data is possible given the specific devices, whether there is actually data to be transferred between the two devices, if the target device already has the data to be transferred stored into it, and what processing/formatting needs to occur before the target device can accept the data. Finally, the actual transfer of data must be initiated either by medical staff or automatically by the device, but ultimate control of the data transfer will always be under the control of the medical staff.

Figure 3:
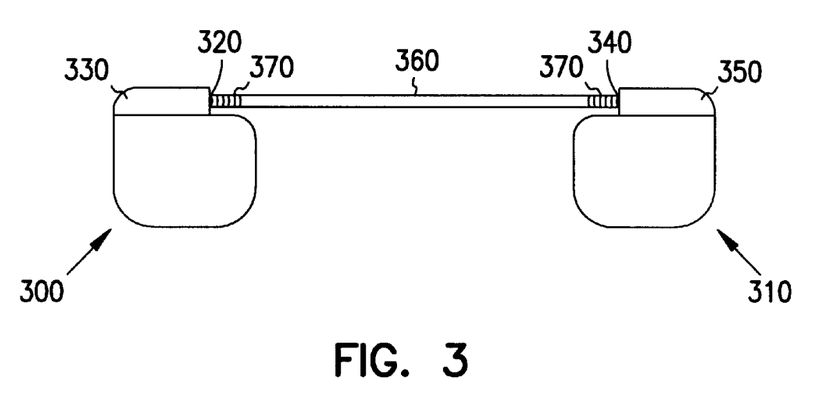
FIG. 3 is a schematic view of two implantable pulse generators coupled via a communication cable according to one embodiment of the present subject matter.

FIG. 3 shows one example of a direct communication link between a first and a second pulse generator. The first implantable pulse generator 300 has been removed from the patient's body. A communication link is established to the second implantable pulse generator 310 by electronically coupling implantable pulse generators through terminals within the connector blocks of the implantable pulse generators 300 and 310, where the terminals are coupled to the electronic circuitry with the implantable pulse generators. In one embodiment, the first implantable pulse generator 300 is electronically coupled to the second implantable pulse generator 310 through establishing a connection between the terminals in the connector port 320 in a first connector block 330 of the first implantable pulse generator 300 and connector port 340 in a second connector block 350 of the second implantable pulse generator 310.

In one embodiment, the first and second implantable pulse generators 300 and 310 are electronically coupled using a conductor cable 360 having lead connectors 370 at each end of the conductor cable 360. The conductor cable 360 includes one or more electrically insulated wires coupled to the lead connectors 370. The conductor cable 360 is also coated with electrically insulating material as are know in the art. Lead connectors 370 include one or more connection pins (not shown) coupled to the electrically insulated wires. When the lead connectors 370 are inserted into the connector ports 320 and 340, the connection pins make electrical contact with the terminals located with in the connector ports 320 and 340. Once lead connectors 370 have been inserted into the connector ports 320 and 340 and the connection pins have made contact with the terminals, the wire, or wires, within the conductor cable 360 conduct the electronic cardiac data between the first and second implantable pulse generators 300 and 310.

After the first and second pulse generators 300 and 310 have been coupled with the conductor cable 360 a communication link is established between the two pulse generators. Electronic cardiac data can then be transferred from the first implantable pulse generator 300 to the second implantable pulse generator 310. In one embodiment, transferring the electronic cardiac data is controlled through the use of a medical device programmer which is in telemetric communication with either the first implantable pulse generator 300 or the second implantable pulse generator 310. In an alternative embodiment, the medical device programmer can be used to control both the first and second implantable pulse generators in transferring the electronic cardiac data. Alternatively, a first medical device programmer is used to control the first implantable pulse generator and a second medical device programmer is used to control the second implantable pulse generator.

In an additional embodiment, a communication link over which patient specific data can move from the first pulse generator to the second pulse generator can be established through a medical device programmer. Electronics internal to the second pulse generator (the device to receive the patient specific data), or the medical device programmer, would allow at least one mode of operation where communication between the medical device programmer occurs directly through cables coupled to the first and second pulse generators and the medical device programmer.

Figure 4:
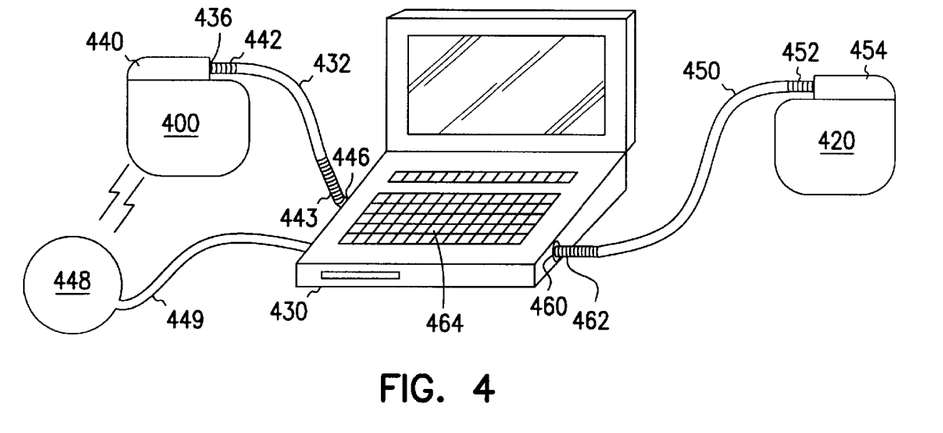
FIG. 4 is a schematic view of two implantable pulse generators coupled via communication cables through a medical device programmer according to one embodiment of the present subject matter.

Referring now to FIG. 4, there is shown one embodiment where a communication link is established between two implantable pulse generators and a medical device programmer. In one embodiment, a first implantable pulse generator 400 is removed from the patient's body. The first implantable pulse generator 400 is then electronically coupled to a medical device programmer 430. In one embodiment, the first implantable pulse generator 400 is coupled to the medical device programmer 430 through a conductor cable 432. In one embodiment, the conductor cable 432 is identical to the conductor cable 360 of FIG. 3. The conductor cable 432 is releasably coupled to connector port 436 of a first connector block 440 through the use of lead connector 442. Lead connector 442 includes connector pins which establish an electrical connection with terminals located within the first connector block 440. As previously described, the terminals are electrically coupled to electronic circuitry within the first implantable pulse generator 400.

The conductor cable 432 is also releasably coupled to a first connector port 446 on the medical device programmer 430 through lead connector 443. Lead connector 443 includes connector pins which establish an electrical connection with terminals located within the first connector port 446. The terminals within the first connector port 446 are electrically coupled to electronic circuitry within the medical device programmer 430.

Once the first implantable pulse generator 400 is electronically coupled to the medical device programmer 430, the programmer electronic circuitry is used to retrieve, or download, the electronic cardiac data from the first implantable pulse generator 400. Commands to retrieve the electronic cardiac data are initiated by the physician or staff through the medical device programmer 430 by keyboard input (or touch-screen or mouse device input). In one embodiment, these commands are provided to the first implantable pulse generator 400 via the direct connection cable 432. In an alternative embodiment, the commands are provided over a telemetry link established with the first implanted implantable pulse generator 400 through the use of a programming head 448 which is coupled to the electronic circuitry of medical device programmer 430 through cable 449.

Once the electronic cardiac data has been retrieved from the first implantable pulse generator 400, the medical device programmer 430 is used to transfer, or download, the electronic cardiac data, or a portion of the electronic cardiac data, to the second implantable pulse generator 420. In one embodiment, the second implantable pulse generator 420 is electronically coupled to the medical device programmer 430.

In one embodiment, the second implantable pulse generator 420 is coupled to the medical device programmer 430 through a conductor cable 450. The conductor cable 450 is releasably coupled to a second connector port 460 on the medical device programmer 430 through lead connector 462. Lead connector 462 includes connector pins which establish an electrical connection with terminals located within the second connector port 460. The terminals within the second connector port 460 are electrically coupled to electronic circuitry within the medical device programmer 430.

The conductor cable 450 is also releasably coupled to connector port 452 of a second connector block 454 through the use of lead connector 450. Lead connector 450 includes connector pins which establish an electrical connection with terminals located within the second connector block 454. As previously described, the terminals are electrically coupled to electronic circuitry within the second implantable pulse generator 420.

In an alternative embodiment, the electronic cardiac data can first be retrieved from the first implantable pulse generator 400 through the use of a telemetric link as previously described. The electronic cardiac data can then be transferred, or downloaded, to the second implantable pulse (generator 420 through the conductor cable 450 as previously described.

Alternatively, only a single connector port (e.g., connector port 446) is provided on the medical device programmer 430. The first implantable pulse generator 400 could then be coupled to the medical device programmer 430 through the signal connector port and the cardiac data transferred from the pulse generator. The first implantable pulse generator 400 would then be uncoupled from the medical device programmer 430 and the second implantable pulse generator 420 would be coupled to the medical device programmer 430 through the signal connector port. The cardiac data (some, all, processed or unprocessed) could then be downloaded into the second implantable pulse generator 420.

Figure 5:
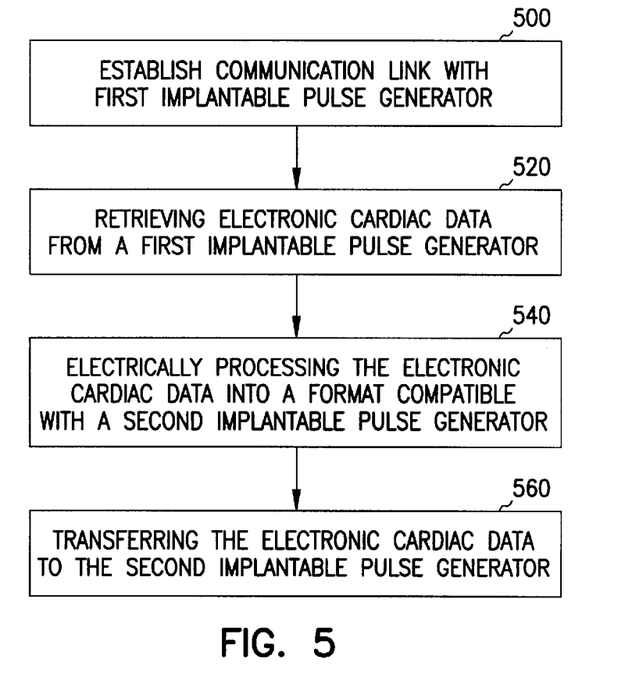
FIG. 5 is a flow chart illustrating one embodiment of the present subject matter.

Referring now to FIG. 5, there is shown an additional embodiment of electronically transferring electronic cardiac data according to the present subject matter. At 500, a communication link is established with the first implantable pulse generator. In one embodiment, the communication link is established through the use of the medical device programmer as previously described. The medical device programmer is then used to retrieve electronic cardiac data from the first implantable pulse generator at 520.

After electronic cardiac data has been retrieved, the medical device programmer is used to electronically format, or process, the electronic cardiac data, including the patient specific data, into a format compatible with the second implantable pulse generator at 540. In one embodiment, the patient specific data is formatted, or computed, to place it into a form that is compatible to be used within the second pulse generator. As the technology incorporated into the second pulse generator is typically more advanced than that used in the first pulse generator, new features and operations have most likely been incorporated into the second pulse generator that are not included in the first pulse generator. In addition, the first pulse generator and the second pulse generator may use different portions of the patient specific data. Additionally, the second pulse generator may use different and/or new combinations of patient specific data not used in the first pulse generator. Thus, processing the patient specific data would reformat the data and reconfigure it (to the extent required or possible) for use with the adaptation and/or historic features of the second pulse generator.

An alternative type of data processing is to improve the efficiency of the stored information or of the second pulse generator as it uses the information. For example, some forms of patient specific adaptation by the pulse generator involve the establishment of a record of different electrophysiologic features that have been previously observed in the patient. Each time a feature was detected, it would be compared to the electrophysiologic feature records to determine if the feature was a new feature or a previously observed feature, where new features are added to the record. A performance advantage is achieved when the order of the features in the record is arranged based on the relative frequency of occurrence, with the order of the features being from the most to the least frequent. In an additional example, performance is improved by removing features from the record that have become outdated, erroneous, or otherwise of little importance.

At 560, the processed patient specific data is then transferred to the second pulse generator. In one embodiment, transferring the patient specific data from the external device occurs over a telemetry channel as previously described, except that the digital data representing the patient specific data will be downloaded into the second pulse generator. Alternatively, patient specific data is transferred through cable connections between the external programmer and the second pulse generator.

In an alternative embodiment, patient specific data from the first pulse generator is processed as previously discussed. In this embodiment, however, the first pulse generator is not being replaced. Instead, the data is being processed to improve the operation of the first pulse generator. In one embodiment, the processed patient specific data overwrites the original patient specific data. Alternatively, the processed patient specific data is added to the first pulse generator to be used with preexisting, updated, or new programs added to the first pulse generator.

Figure 6:
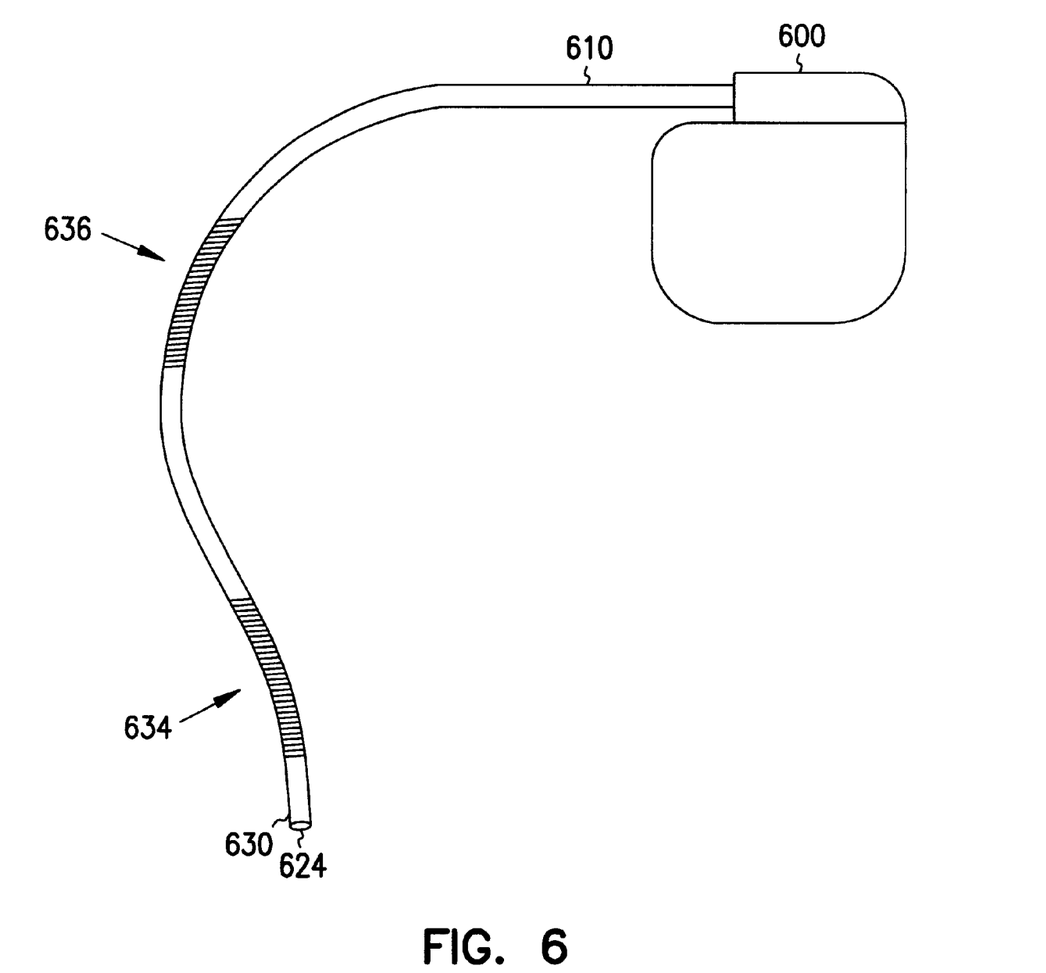
FIG. 6 is a schematic view of one embodiment of an implantable pulse generator.

Referring now to FIG. 6, there is shown one embodiment of an implantable pulse generator according to the present subject matter. FIG. 6 shows an implantable cardioverter-defibrillator (ICD) 600 electrically and physically coupled to at least one intracardiac catheter 610. In one embodiment, the intracardiac catheter 610 includes one or more pacing electrodes and one or more intracardiac defibrillation electrodes.

In one embodiment, the intracardiac catheter 610 is an endocardial lead adapted to be releasably attached to the ICD 600. The intracardiac catheter 610 has an elongate body with a pacing electrode 624 located at, or adjacent, a distal end 630 of the intracardiac catheter 610. In one embodiment, the pacing electrode 624 is a tip electrode positioned at the distal end 630 of the intracardiac catheter 610. Alternatively, the pacing electrode 624 is an annular, or a semi-annular ring electrode positioned adjacent the distal end 630.

The intracardiac catheter 610 also includes one or more defibrillation electrodes. In one embodiment, the intracardiac catheter 610 has a first defibrillation electrode 634 and a second defibrillation electrode 636, where the first defibrillation electrode 634 and the second defibrillation electrode 636 are defibrillation coil electrodes as are known in the art.

Figure 7:
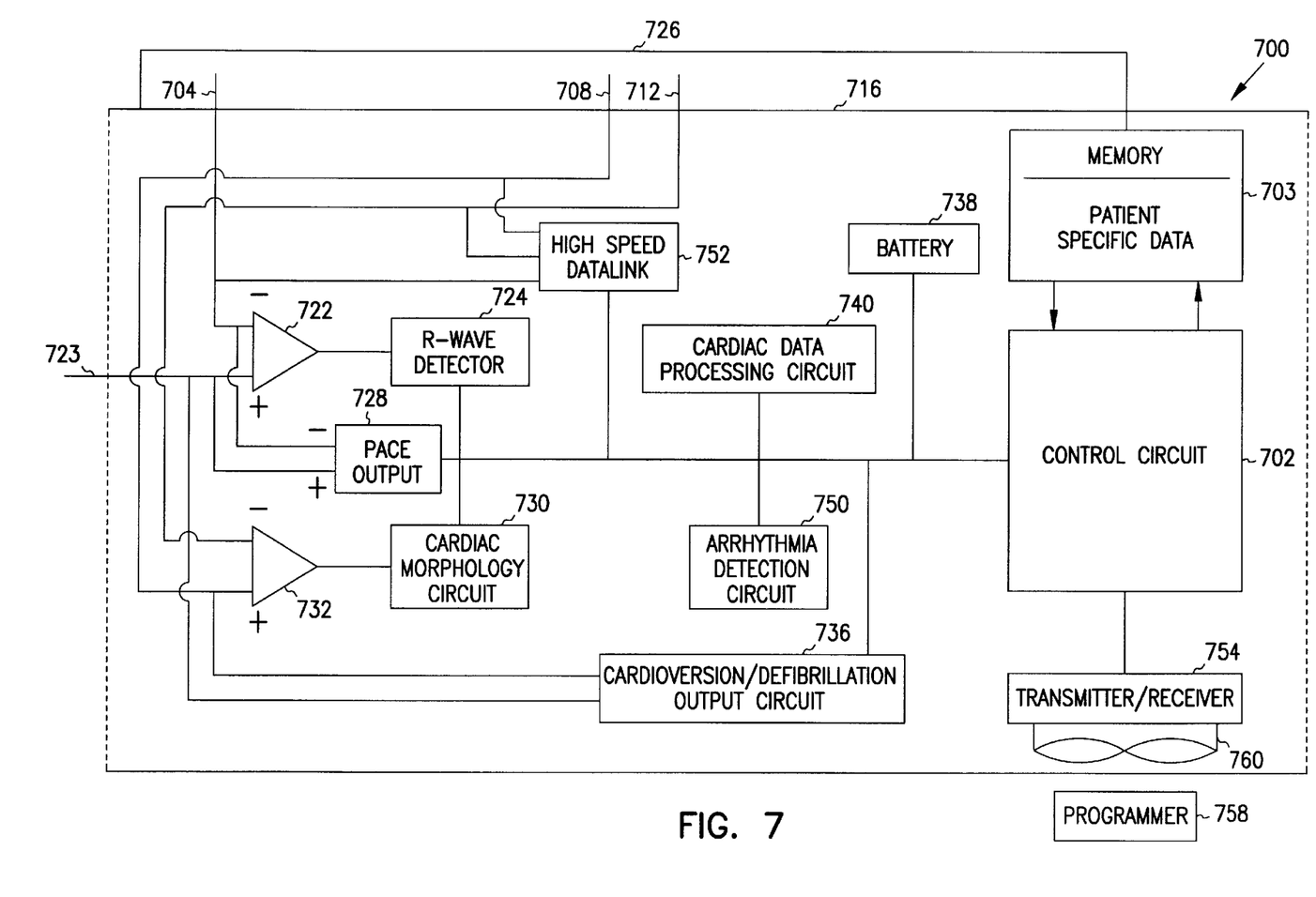
FIG. 7 is a block diagram of an implantable pulse generator according to one embodiment of the present subject matter.

Referring now to FIG. 7, there is shown an embodiment of a block diagram of an ICD 600. The ICD 600 includes electronic control circuitry 700 which receives one or more electronic cardiac signals from the heart 620 (FIG. 6) and under predetermined conditions delivers electrical energy to the heart 620.

In one embodiment, the electronic control circuitry 700 is a programmable microprocessor-based system, with a control circuit 702 and a memory circuit 703, which contains parameters for various pacing and sensing modes and stores both data indicative of cardiac signals received by the electronic control circuitry 700 and patient specific data as previously discussed. The electronic control circuitry 700 further includes terminals labeled with reference numbers 704, 708, and 712 for connection to the electrodes attached to the surface of the intracardiac catheter 610. The pacing electrode 624 is electrically connected to terminal 704 and to the electronic control circuitry 700 through an electrically insulated conductor provided within the elongate body of the intracardiac catheter 610. The first defibrillation electrode 634 and the second defibrillation electrode 636 are connected to terminals 708 and 712, respectively, and to the electronic control circuitry 700 through electrically insulated conductors provided within the elongate body of the intracardiac catheter 610.

The electronic control circuitry 700 is encased and hermetically sealed in a housing 716 suitable for implanting in a human body. In one embodiment, the housing 716 is made of titanium, however, other biocompatible housing materials as are known in the art may be used. A connector block 726 is additionally attached to the housing 716 to allow for the physical and the electrical attachment of the intracardiac catheter 610 and the electrodes to the ICD 600 and the encased electronic control circuitry 700. In addition, the connector block 726 allows for the conductor cable(s) to be physically coupled to the ICD 600 so that the electronic control circuitry 700 can be electrically coupled to either the electronic circuitry within the external programmer or the electronic control circuitry within a second ICD.

Sense amplifier 722 is coupled to the electronic control circuitry 700, and is electrically coupled to the connected at terminal 704 to received cardiac signals from the pacing electrode 624. In addition, the housing 716 of the ICD 600 is also coupled to the sense amplifier 722 at 723 to allow for unipolar cardiac rate sensing between the pacing electrode 624 and the housing 716. Alternatively, the input to the sense amplifier 722 is from connection terminal 708 to allow for bipolar sensing and pacing between the pacing electrode 624 and the first defibrillation electrode 634. The output of the sense amplifier 722 is shown connected to an R-wave detector 724. These components serve to sense, amplify and analyze the morphological features of the cardiac cycle from the ventricular regions and apply signals indicative thereof to the control circuit 702. Among other things, the control circuit 702 responds to the R-wave detector 724 by providing pacing signals to a pace output circuit 728 via bus 730, as needed according to the programmed pacing mode. Pace output circuit 728 provides output pacing signals to terminals 704 and 723, which connect to the pacing electrode 624 and the housing 716 for cardiac pacing.

The first defibrillation electrode 634 and the second defibrillation electrode 636 are coupled to a sense amplifier 732, whose output is connected to a cardiac morphology circuit 734. These components serve to sense and amplify the QRS-waves of the cardiac cycle from the ventricular region of the heart 26, and apply signals indicative thereof to the control circuit 702 and the arrhythmia detection circuit 750. In one embodiment, the arrhythmia detection circuit receives and analyzes cardiac signals for the occurrence of tachyarrhythmias, including fibrillation. The control circuit 702 responds to signals received from the arrhythmia detection circuit 750 and the cardiac signals sensed within the heart using the intracardiac catheter 610 by providing signals to cardiovertion/defibrillation output circuitry 736 to provide either cardiovertion or defibrillation electrical energy to the heart depending upon nature of the arrhythmia sensed by the arrhythmia detection circuit 750. Power to the ICD 600 is supplied by an electrochemical battery 738 that is housed within the ICD 600.

The electronic control circuitry 700 further includes a cardiac-data-processing circuit 740, which is electrically coupled to the R-wave detector 724, the cardiac morphology circuit 734, a communication circuit (elaborated on below)

and the arrhythmia detection circuit 750. In one embodiment, the cardiac-data-processing circuit 740 receives signals from the aforementioned circuits and produces patient-specific data from the output of these circuits. The patient-specific data calculated and analyzed by the cardiac data processing circuit 740 is then delivered to the control circuit 702 which stores the patient specific data in the memory 703. Examples of such patient specific data would include the averages, variances, and historic trends in QRS width or QT intervals derived from the morphological signals from the cardiac morphology circuitry 734 or averages, variances, and historic trends in the heart rate derived from the R-wave detection 724.

In an alternative embodiment, the cardiac-data-processing circuit 740 receives electronic cardiac data from an implantable pulse generator, or a medical device programmer, through the communication circuit. The cardiac-data-processing circuit 740 then formats the electronic cardiac data into a format that is compatible with the implantable pulse generator in which the cardiac-data-processing circuit is operating. In one embodiment, the cardiac-data-processing circuit 740 processes patient specific cardiac data into a format to be used in the arrhythmia detection circuit 750 within the electronic control circuitry 700.

The electronic control circuitry 700 further includes a communication circuit to receive and transmit electronic-cardiac data between a first implantable pulse generator and a second implantable pulse generator. In one embodiment, the communication circuit is a high-speed datalink 752 which is coupled to terminals 704, 708 and 712 to allow for data to be received and transmitted. In one embodiment, the high-speed datalink 752 allows for direct communication with the programmer or another device. The high-speed datalink 752 is coupled to the data bus 730 to allow for control of the high-speed datalink 752 by the control circuit 702. Additionally, the high-speed datalink 752 is coupled via the bus 730 to the memory 703 to allow for data to be retrieved from and programmed into the memory 703. In an alternative embodiment, the communication circuit is a telemetric transmitter/receiver 754 which is coupled to the control circuit 702. The telemetric transmitter/receiver 754 can communicate with an external controller 758 over a radio frequency channel transmitted and received by wire loop antenna 760.

In one embodiment, when the ICD 600 is used to retrieve patient specific cardiac data from either a medical device programmer or another ICD, commands to retrieve the patient specific data are received through either the high-speed datalink 752 or the communication circuitry 754. In one embodiment, the commands are provided by a medical device programmer in communication with the ICD 600. After the commands have been received, the control circuit 702 provides commands to direct either the high-speed datalink 750 or the electronic communication circuitry 754 to transmit commands requesting cardiac data from either the medical device programmer or the ICD being replaced. Once the cardiac data has been received by the ICD 600, the control circuit 702 is used to place the cardiac data into a form to be used by the ICD 600.

Figure 8:
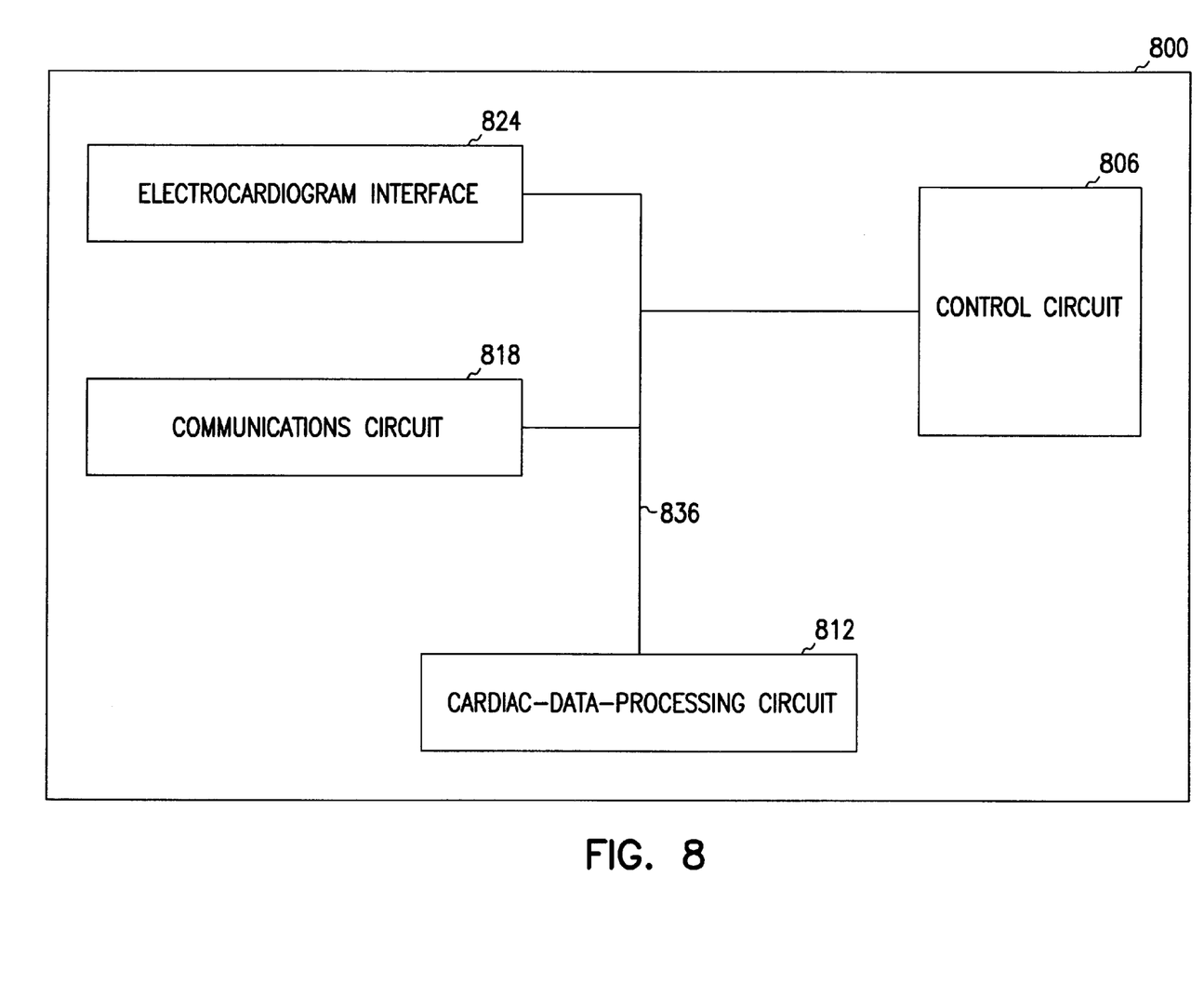
FIG. 8 is a block diagram of a medical device programmer according to one embodiment of the present subject matter.

Referring now to FIG. 8, there is shown a block diagram of a medical device programmer 800 according one embodiment of the present subject matter. In one embodiment, the medical device programmer 800 is a microprocessor based system which includes, among other things, a control circuit 806, a cardiac-data-processing circuit 812, at least one communication circuit 818, and an electrocardiogram interface 824. The circuits are interconnected by data bus 836 to allow for data and command signals to be transferred between the individual circuits.

The control circuit 806 is coupled to at least one communication circuit 818 and the cardiac-data-processing circuit 812. In one embodiment, the control circuit 806 controls at least one communication circuit 818 to receive electronic-cardiac data from the first implantable pulse generator and to transmit the formatted electronic-cardiac data to the second implantable pulse generator.

At least one communication circuit 818 receives and transmits electronic-cardiac data between the medical device programmer and a first implantable pulse generator. Additionally, at least one communication circuit 818 receives and transmits electronic-cardiac data between the first implantable pulse generator and the second implantable pulse generator, as previously described. In one embodiment, the communication circuit 818 includes a high-speed datalink channel to receive and transmit electronic cardiac data. The high-speed datalink channel is coupled to the control circuit 806 which controls the operation of the high-speed datalink channel to receive and transmit commands and electronic cardiac data, including patient specific data. In one embodiment, the high-speed datalink channel is used to receive commands and patient specific data from a first implantable pulse generator and to transmit formatted electronic-cardiac data (explained below) to a second implantable pulse generator.

The communication circuit 818 can further include a telemetry interface circuit (as previously described) to allow for electronic cardiac data to be received and transmitted via a telemetric link. Telemetry interface circuit is physically and electrically coupled to a programming head (now shown) of the medical device programmer through a cable. The telemetry interface circuit allows the medical device programmer to communicate with an implanted pulse generator in order to retrieve patient specific data from the implanted device. Patient specific data gathered from the first implantable pulse generator can then be stored and formatted by the medical device programmer 800 before some or all of the patient specific data is transferred to the second implantable pulse generator. Alteratively, the telemetry interface circuit is used to control one or more of the implantable pulse generators during the transfer of patient specific data between the two devices.

The cardiac-data-processing circuit 812 is coupled to the communication circuit 818, wherein the cardiac-data-processing circuit 812 receives electronic cardiac data from an implantable pulse generator through the communication circuit. In one embodiment, the cardiac-data-processing circuit 812 receives electronic cardiac data from the first implantable pulse generator. The cardiac-data-processing circuit 812 then formats the electronic cardiac data from the first implantable pulse generator to a format that is compatible with a second implantable pulse generator.

In one embodiment, the programmable features of the second implantable pulse generator are provided to the cardiac-data-processing circuit 812. The cardiac-data-processing circuit 812 then analyzes the patient specific data received from the first implantable pulse generator to calculate programmable values and patient specific data to be supplied to the second medical device. In one embodiment, the programmable values and the patient specific data to be supplied to the second medical device are calculated, formatted and then displayed on the medical device program display screen for approval by the physician. In one embodiment, it is at this point that changes and or additional programming information for the second implantable pulse generator can be supplied to the medical device programmer 800. The ECG interface circuit 824 is coupled to the microprocessor 806 through data bus 836. The ECG interface circuit 824 allows the programmer to acquire and present patient surface electrograms on the same recordings or paper tracings as the rate and morphology electrograms that are sensed by the device.

In addition, the medical device programmer 800 can include additional interfaces not shown. For example, the medical device programmer 800 further includes circuitry and an interface for correcting to and operating a printer, analog output for allowing electrocardiogram signals to be recorded, data input devices (such as alphanumeric keyboard and computer mouse) and video input/output circuitry coupled to a display monitor on the medical device programmer 800 to allow for commands to be entered into the medical device programmer 800 and for messages about the operation of the medical devices and the programmer to be displayed.

We claim:

1. A method, comprising:
    establishing a communication link with a first implantable pulse generator;
    retrieving electronic cardiac data stored in the first implantable pulse generator through the communication link; and
    electronically downloading the electronic cardiac data to a second implantable pulse generator.

2. The method of claim 1, wherein electronically downloading the electronic cardiac data to the second implantable pulse generator includes transferring the electronic cardiac data from the first implantable pulse generator to a medical device programmer; and
    transferring the electronic cardiac data from the medical device programmer to the second implantable pulse generator.

3. The method of claim 2, wherein transferring the electronic cardiac data from the medical device programmer to the second implantable pulse generator is over a telemetric communication link.

4. The method of claim 2, wherein transferring the electronic cardiac data from the first implantable pulse generator to the medical device programmer is over a telemetric communication link.

5. The method of claim 2, including electronically processing the electronic cardiac data in the medical device programmer into a format compatible with the second implantable pulse generator.

6. The method of claim 2, wherein transferring the electronic cardiac data includes directly coupling the first implantable pulse generator and the second implantable pulse generator to the medical device programmer.

7. The method of claim 1, wherein electronically downloading the electronic cardiac data to a second implantable pulse generator includes directly transferring the electronic cardiac data from the first implantable pulse generator to the second implantable pulse generator.

8. The method of claim 7, including coupling the first implantable pulse generator to the second implantable pulse generator through at least one connector port in a first connector block of the first implantable pulse generator and a second connector block of the second implantable pulse generator.

9. The method of claim 7, including controlling the transfer of the electronic cardiac data with a medical device programmer.

10. A method, comprising:
    retrieving patient specific data from a first implantable pulse generator, wherein patient specific data includes data generated from cardiac signals sensed by the first implantable pulse generator;
    electronically processing the patient specific data into a format compatible with a second implantable pulse generator; and
    transferring the patient specific data to the second implantable pulse generator.

11. The method of claim 10, including sensing cardiac signals representative of electrical cardiac activity with the first implantable pulse generator;
    determining patient specific data in the first implantable pulse generator from the sensed cardiac signals; and
    storing the patient specific data in the first implantable pulse generator.

12. The method of claim 10, wherein transferring the patient specific data includes directly transferring the patient specific data from the first implantable pulse generator to the second implantable pulse generator.

13. The method of claim 12, including coupling the first implantable pulse generator to the second implantable pulse generator through at least one connector port in a first connector block of the first implantable pulse generator and at least one connector port in a second connector block of the second implantable pulse generator.

14. The method of claim 13, including controlling the transfer of the patient specific data with a medical device programmer.

15. The method of claim 10, where transferring the patient specific data includes transferring the patient specific data from the first implantable pulse generator to a medical device programmer; and
    transferring the patient specific data from the medical device programmer to the second implantable pulse generator.

16. The method of claim 15, wherein transferring the patient specific data from the medical device programmer to the second implantable pulse generator is over a telemetric communication link.

17. The method of claim 15, wherein transferring the patient specific data from the first implantable pulse generator to the medical device programmer is over a telemetric communication link.

18. The method of claim 15, wherein transferring the electronic cardiac data includes directly coupling the first implantable pulse generator and the second implantable pulse generator to the medical device programmer.

19. A system, comprising:
    a communication circuit to receive and transmit electronic-cardiac data between a first implantable pulse generator and a second implantable pulse generator;
    a cardiac-data-processing circuit coupled to the communication circuit, wherein the cardiac-data-processing circuit receives electronic cardiac data from the first implantable pulse generator through the communication circuit and formats the electronic cardiac data from the first implantable pulse generator to a format compatible with the second implantable pulse generator; and
    a control circuit coupled to the communication circuit and the cardiac-data-processing circuit, wherein the control circuit controls the communication circuit to receive electronic-cardiac data from the first implantable pulse generator and to transmit formatted electronic-cardiac data to the second implantable pulse generator.

20. The system of claim 19, wherein the communication circuit includes at least one high-speed datalink channel for transmission and reception of electronic cardiac data.

21. The system of claim 19, wherein the communication circuit includes a telemetry interface circuit, wherein the telemetry interface circuit transmits and receives electronic cardiac data on a radio frequency channel.

22. The system of claim 19, wherein the communication circuit, the cardiac data processing circuit and the microprocessor are included in an implantable pulse generator.

23. The system of claim 19, wherein the communication circuit, the cardiac data processing circuit and the microprocessor are included in a medical device programmer.

* * * * *